(12) United States Patent
Brian, III et al.

(10) Patent No.: US 10,940,035 B2
(45) Date of Patent: *Mar. 9, 2021

(54) DEVICES, SYSTEMS AND METHODS FOR RAPID ENDOVASCULAR COOLING

(71) Applicant: ZOLL Circulation, Inc., San Jose, CA (US)

(72) Inventors: Ben F. Brian, III, Menlo Park, CA (US); Scott D. Wilson, Woodside, CA (US)

(73) Assignee: Zoll Circulation, Inc., San Jose, CA (US)

( * ) Notice: Subject to any disclaimer, the term of this patent is extended or adjusted under 35 U.S.C. 154(b) by 256 days.

This patent is subject to a terminal disclaimer.

(21) Appl. No.: 15/953,116

(22) Filed: Apr. 13, 2018

(65) Prior Publication Data

US 2018/0360651 A1 Dec. 20, 2018

Related U.S. Application Data

(63) Continuation of application No. 14/571,044, filed on Dec. 15, 2014, now Pat. No. 9,943,438, which is a
(Continued)

(51) Int. Cl.
*A61F 7/12* (2006.01)
*A61M 25/10* (2013.01)
*A61F 7/00* (2006.01)

(52) U.S. Cl.
CPC ........... *A61F 7/12* (2013.01); *A61M 25/1002* (2013.01); *A61M 25/1011* (2013.01);
(Continued)

(58) Field of Classification Search
CPC ....... A61F 7/12; A61F 7/123; A61F 2007/126
See application file for complete search history.

(56) References Cited

U.S. PATENT DOCUMENTS 3,504,674 A 4/1970 Swenson et al.
4,173,228 A 11/1979 Van Steenwyck et al.
(Continued)

FOREIGN PATENT DOCUMENTS

WO WO 97/06845 A1 2/1997
WO WO 98/24491 A1 6/1998
(Continued)

OTHER PUBLICATIONS

Supplementary European Search Report dated Jul. 1, 2010 in related European Application No. EP 06774480.
(Continued)

*Primary Examiner* — Kaitlyn E Smith
(74) *Attorney, Agent, or Firm* — Fish & Richardson P.C.

(57) ABSTRACT

Devices and methods for warming or cooling blood flowing through the vasculature of a human or animal subject so as to alter or control the temperature of all or part of the subject's body. Heat exchangers are positioned within the subject's vasculature and heated or cooled heat exchange fluid is circulated through the heat exchanger. For certain therapeutic applications, the heat exchanger and associated elements of the system have sufficient power to lower the subject's body temperature by at least 3 degrees C. in less than 30 minutes.

21 Claims, 7 Drawing Sheets

Related U.S. Application Data continuation of application No. 11/479,961, filed on Jun. 29, 2006, now Pat. No. 8,911,485.

(60) Provisional application No. 60/695,786, filed on Jun. 29, 2005.

(52) U.S. Cl.
CPC . *A61F 2007/0056* (2013.01); *A61F 2007/126* (2013.01); *A61M 2025/1072* (2013.01); *A61M 2205/36* (2013.01); *A61M 2205/3606* (2013.01); *A61M 2205/366* (2013.01)

(56) References Cited

U.S. PATENT DOCUMENTS

| | | | |
|---|---|---|---|
| 4,562,846 A | 1/1986 | Cox et al. | |
| 5,895,418 A | 4/1999 | Saringer | |
| 6,231,594 B1 | 5/2001 | Dae | |
| 6,572,640 B1 | 6/2003 | Balding et al. | |
| 6,582,457 B2 | 6/2003 | Dae et al. | |
| 6,610,083 B2 | 8/2003 | Keller et al. | |
| 6,645,234 B2 | 11/2003 | Evans et al. | |
| 6,682,551 B1 | 1/2004 | Worthen et al. | |
| 6,702,839 B1 | 3/2004 | Dae et al. | |
| 6,716,236 B1 | 4/2004 | Tzeng et al. | |
| 6,887,263 B2 | 5/2005 | Bleam et al. | |
| 7,008,444 B2 | 3/2006 | Dae et al. | |
| 7,510,569 B2 | 3/2009 | Dae et al. | |
| 7,566,341 B2 | 7/2009 | Keller et al. | |
| 8,911,485 B2 * | 12/2014 | Brian, III | A61M 25/1011 607/105 |
| 9,943,438 B2 * | 4/2018 | Brian, III | A61M 25/1002 |
| 2002/0111657 A1 | 8/2002 | Dae et al. | |
| 2002/0183692 A1 * | 12/2002 | Callister | A61F 7/123 604/113 |
| 2003/0195597 A1 * | 10/2003 | Keller | A61F 7/123 607/105 |
| 2004/0133256 A1 * | 7/2004 | Callister | A61F 7/123 607/105 |
| 2004/0199230 A1 | 10/2004 | Yon | |
| 2005/0027290 A1 | 2/2005 | Dae et al. | |
| 2005/0080374 A1 | 4/2005 | Esch et al. | |
| 2009/0043366 A1 | 2/2009 | Dae | |
| 2009/0254161 A1 | 10/2009 | Dae et al. | |
| 2010/0030307 A1 | 2/2010 | Keller et al. | |

FOREIGN PATENT DOCUMENTS

| | | |
|---|---|---|
| WO | WO 00/009054 A1 | 2/2000 |
| WO | WO 01/10365 A1 | 2/2001 |

OTHER PUBLICATIONS

USPTO Office Action dated Jun. 7, 2010 in related U.S. Appl. No. 11/479,961, filed Jun. 29, 2006, now U.S. Pat. No. 8,911,485.

USPTO Final Office Action dated Feb. 18, 2011 in related application U.S. Appl. No. 11/479,961, filed Jun. 29, 2006, now U.S. Pat. No. 8,911,485.

USPTO Office Action dated Jul. 31, 2012 in related U.S. Appl. No. 11/479,961, filed Jun. 29, 2006, now U.S. Pat. No. 8,911,485.

USPTO Final Office Action dated Apr. 22, 2013 in related U.S. Appl. No. 11/479,961, filed Jun. 29, 2006, now U.S. Pat. No. 8,911,485.

Office Action dated Apr. 21, 2015 in corresponding Japanese Patent Application No. 2013-128883.

USPTO Office Action dated May 17, 2017 in related U.S Appl. No. 14/571,044, filed Dec. 15, 2014, now U.S. Pat. No. 9,943,438.

* cited by examiner

DEVICES, SYSTEMS AND METHODS FOR RAPID ENDOVASCULAR COOLING

RELATED APPLICATION

This patent application is a continuation of copending U.S. patent application Ser. No. 14/571,044 filed Dec. 15, 2014 and issuing as U.S. Pat. No. 9,943,438 on Apr. 17, 2018, which is a continuation of U.S. patent application Ser. No. 11/479,961 filed Jun. 29, 2006 and issued as U.S. Pat. No. 8,911,485 on Dec. 16, 2014, which claims priority to U.S. Provisional Patent Application No. 60/695,786 filed on Jun. 29, 2005, the entire disclosure of each such prior application and patent being expressly incorporated herein by reference.

FIELD OF THE INVENTION

This invention relates generally to devices and methods for medical treatment and more particularly to devices and methods for endovascular heat exchange for altering or controlling body temperature in a human or animal subject.

BACKGROUND OF THE INVENTION

Therapeutic hypothermia can protect various tissues, including cardiac, brain, and renal tissue, against the effects of ischemic, anoxic or toxic insult. For example, animal studies and/or clinical trials suggest that mild hypothermia can have neuroprotective and/or cardioprotective effects in animals or humans who suffer from ischemic cardiac events (e.g., myocardial infract, acute coronary syndromes, etc.), postanoxic coma after cardiopulmonary resuscitation, traumatic brain injury, stroke, subarachnoid hemorrhage, fever and neurological injury. Also, studies have shown that whole body hypothermia can ameliorate the toxic effects of radiographic contrast media on the kidneys (e.g., radiocontrast nephropathy) of patients with pre-existing renal impairment who undergo angiography procedures.

One method for inducing hypothermia is through the use of a technique known as endovascular temperature management (ETM). In ETM, a catheter having a heat exchanger is inserted into a blood vessel and thermal exchange fluid of precisely controlled temperature is circulated through the catheter's heat exchanger. This technique can effectively cool blood flowing through the subject's vasculature and, as a result, lower the core body temperature of the subject to some desired target temperature. ETM is also capable of warming the body and/or of controlling body temperature to maintain a monitored body temperature at some selected temperature. If a controlled rate of re-warming or re-cooling from the selected target temperature is desired, that too can be accomplished by carefully controlling the amount of heat added or removed from the body and thereby controlling the temperature change of the patient.

For ischemic events that result from blockage of an artery, such as myocardial infarction and ischemic stroke, a primary treatment objective is to remove, dissolve or bypass the arterial blockage so as to reperfuse the ischemic tissue within a shot period of time (e.g., less than 5 hours) after the onset of acute clinical symptoms. Such reperfusion can be accomplished by surgery (e.g., open embolectomy, bypass grafting, etc.), catheter based intervention (e.g., angioplasty, stenting, atherectomy, catheter-based embolectomy, etc.) or through the use of thrombolytic drugs (e.g., tissue plasminogen activator (TPA) or streptokinase). Because of the tissue protection added by hypothermia, it is currently believed that optimal treatment of such ischemic events may be achieved through a combination of therapeutic hypothermia with a reperfusion strategy such as surgery, catheter based intervention and/or thrombolytic drug therapy.

The effects of mild whole body hypothermia have been studied in acute myocardial infarction patients who subsequently underwent coronary interventions (i.e., angioplasty and stenting procedures) which resulted in reperfusion of the infracted myocardium. In at least one study, it was observed that patients with anterior wall infarctions whose core body temperature had been lowered to at least 35° C. prior to reperfusion had significantly smaller median infarct size than other patients with anterior wall infarctions whose core body temperature was greater than 35° C. at the time of reperfusion. This observation is not explained by other factors including time-to-presentation, lesion location and incidence of TIMI flow prior to angioplasty.

Thus, at least in the treatment of evolving myocardial infarctions, the size of the infarct may be significantly reduced if mild hypothermia is induced prior to reperfusion. Given the motivation to accomplish reperfusion as rapidly as possible, there exists a need in the art for the development of new methods, devices and systems for rapid endovascular cooling to facilitate the induction of hypothermia prior to reperfusion in subjects suffering from ischemic disorders such as myocardial infarction or ischemic stroke. Beyond this example, it should be understood that such methods, devices and systems are also beneficial in other therapeutic applications including but not limited to the treatment of cardiac arrest, radiocontrast nephropathy, inotropic treatment of heart disease, and others.

Furthermore, the mammalian body has physiologic temperature regulation mechanisms that function to maintain a setpoint temperature (usually normothermia) under most conditions. These innate physiologic mechanisms also cause the body to warm faster if the body is perceived to be cold and to cool faster if the body is perceived to be warm. Conscious subjects who have not been medicated to deter sivering may often times shiver in response to a decrease in their body temperature. Such shivering can provide significant additional energy which must be overcome in order to induce the hypothermic effect. Strategies to prevent shivering include warming blankets applied to the skin of the patient as well as several drugs such as those described in U.S. Pat. No. 6,231,594 (Dae), U.S. Pat. No. 6,582,457 (Dae), U.S. Pat. No. 6,702,839 (Dae) and U.S. Pat. No. 7,008,444 (Dae), each such United States Patent being expressly incorporated herein by reference. The development of a new endovascular heat exchange catheter system with substantially more cooling (or warming power) could provide a new treatment that is better able to override the body's normal physiologic mechanisms and external factors thereby inducing therapeutic hypothermia (or hyperthermia) faster than endovascular heat exchange catheter systems of the prior art. Likewise, such more efficient endovascular heat exchange catheter system would be better able to control temperature change in the face of the body's own mechanism that might be attempting to change the body's temperature back to the set point after a period of hypothermia, for example maintaining a desired temperature that is other than the set point temperature, or re-warming a cold patient back to normothermia at a very controlled rate that is slower than the rate the body would otherwise warm itself.

SUMMARY OF THE INVENTION

The present invention provides devices, methods and systems useable to rapidly alter the body temperature of a human or animal subject and to then maintain the subject's body temperature within a target temperature range. In at least some embodiments, the devices, methods and systems of the present invention have sufficient cooling power to lower the core body temperature of a normothermic human subject by 3 degrees C. or more (e.g., from a temperature of 37 degrees C. to a temperature or 34 degrees C. or less) within thirty (30) minutes. Thus, the devices, methods and systems of the present invention may be useable to induce cardio-protective, neuro-protective, or renal-protective levels of hypothermia in patients suffering from myocardial infarction and/or ischemic stroke, prior to reperfusion of the ischemic tissues by surgery, catheter-based intervention and/or thrombolytic therapy.

In accordance with the invention, there is provided a heat exchange catheter system that comprises a heat exchange catheter and a fluid cooling apparatus useable to cool a thermal exchange fluid (e.g., 0.9% saline solution) and to circulate that cooled thermal exchange fluid through the heat exchange catheter. The elements of the fluid cooling apparatus and the heat exchange catheter may be cooperatively sized, constructed and configured such that the system is capable of reliably decreasing a conscious patient's temperature 3 degrees Celsius in 30 minutes or less.

Still further in accordance with the invention, there are provided heat exchange catheters that incorporate detectors or other apparatus to facilitate their advancement to a specific location within the vasculature of a human or animal subject to thereby optimize the heat exchanging efficiency of the heat exchange catheter. In some embodiments, optimal heat exchange may be accomplished by ensuring that a heat exchanger mounted on the catheter has been advanced into a particular blood vessel (e.g., the inferior vena cava) and the catheter may incorporate one or more detectors (e.g., graduated distance markings, radiopaque marker bands that are visible under fluoroscopy, apparatus for detecting changes in vessel diameter or anatomy, apparatus for detecting changes in blood flow, etc.) for detecting when the entire heat exchanger has reached a position within the desired blood vessel.

Still further in accordance with the invention, there is provided an endovascular heat exchange device and method wherein heat exchange fluid is circulated through an endovascular heat exchanger in a pulsatile fashion, thereby causing movement of at least a portion of the heat exchanger as the heat exchange fluid circulates therethrough. Such movement disrupts laminarity of blood flow adjacent to the heat exchange surface and/or otherwise results in improved heat exchanged efficiency between the heat exchanger and the subject's blood. In some embodiments, the heat exchanger may comprise a heat exchange balloon having helical lobes through which heated or cooled heat exchange fluid (e.g., 0.9% saline solution) is circulated. In such embodiments the momentum of flow into and within the lobes creates a rotational torque or force which causes rotational movement of the heat exchange balloon. With non-pulsatile flow this rotation would reach a fixed position which would remain essentially constant. However with pulsatile flow, the periodic alteration of the pressure of flow is sufficient to remove/reinitiate the torque on the balloon, creating advantageous movement that enhances heat exchange. The pulsatile flow need not cause substantial deflation of the heat exchange balloon order to effect movement of the heat exchange balloon. Rather, pulsatile flow that remains above the pressure required to maintain the heat exchange balloon in a fully inflated state may be used and may cause substantially rotational movement of the balloon as opposed to repetitive expansion and contraction of the balloon. Those experienced in the art will realize that such pulsatile flow of the heat exchange fluid may be generated with commercially available peristaltic pumps such as those available from Watson-Marlow, or further enhanced with pulsatile control systems such as those used in extracorporeal blood pumps or cardiac assist devices. Further, the heat exchanger balloon or a portion thereof may be pre-tensioned (e.g., twisted to a tensioned state) before being affixed to the catheter body. This pre-tensioning of the heat exchange balloon may serve to exaggerate the movement that the balloon will undergo in response to pulsation of the flow of heat exchange fluid through the balloon.

Still further in accordance with the invention, there is provided an endovascular heat exchange device and method for warming or cooling blood flowing through a blood vessel adjacent to the ostium of a branch vessel in a human or animal subject. In general, this method includes the steps of a) providing a heat exchanger that is positionable in the blood vessel adjacent to the ostium of a branch vessel, said heat exchanger being operative to exchange heat with blood flowing through the blood vessel, said heat exchanger having a circumscribed diameter D while in operation, said heat exchanger being configured to define at least one blood flow channel within the circumscribed diameter D through which blood may either i) enter the blood vessel from the branch vessel or ii) enter the branch vessel from the blood vessel, b) positioning the heat exchanger within the blood vessel adjacent to the ostium of said branch vessel and c) operating the heat exchanger to heat or cool blood flowing through the blood vessel while i) at least some of the blood entering the blood vessel from the branch vessel has flowed through said at least one blood flow channel or ii) at least some of the blood entering the branch vessel from the blood vessel has flowed through said at least one blood flow channel. In some embodiments, the heat exchanger may comprise a helical member through which heat exchange fluid circulates, such helical member having circumscribed inflated diameter D2 and being configured to define a helical blood flow channel through which at least some of the blood entering the blood vessel from the branch vessel has flowed or through which at least some of the blood entering the branch vessel from the blood vessel has flowed.

Still further in accordance with the invention, there is provided a heat exchange balloon having sufficiently thin walls to allow rapid and effective heat exchange across the balloon walls, and yet retaining the advantageous shape that presents a maximum surface area to the blood flowing past the balloon and a minimal restriction of blood flowing past the balloon. The balloon is also capable of sufficient collapse under vacuum to present a minimal insertion profile, yet expand sufficiently when inflated to provide a large and effective heat exchange balloon.

Still further in accordance with the invention, any details, aspects, elements or attributes of one of the above-summarized embodiments may be combined or replaced by any aspects, elements or attributes of another embodiment, unless doing so would render the resultant embodiment inoperative or unusable for its intended purpose.

Further details, aspects, elements and attributes of the present invention may be appreciated by those of skill in the art after reading the detailed description and examples set forth below.

DETAILED DESCRIPTION OF THE DRAWINGS

FIG. 3A is an enlarged view of segment 3A of FIG. 3 showing an example of the manner in which heat exchange fluid may flow therethrough.

Figure 4A:
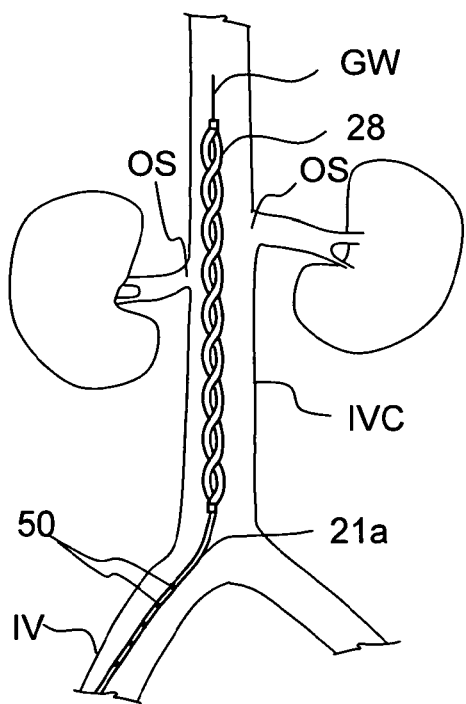

FIG. 4A is a diagram of the inferior vena cava and iliac bifurcation of a human subject with a heat exchange catheter of the present invention inserted therein, such heat exchange catheter having optional distance markings that correlate to the subject's body size/vascular anatomy so as to be useable to determine when substantially the entire heat exchange balloon has been advanced through the iliac vein and into the inferior vena cava.

Figure 4B:
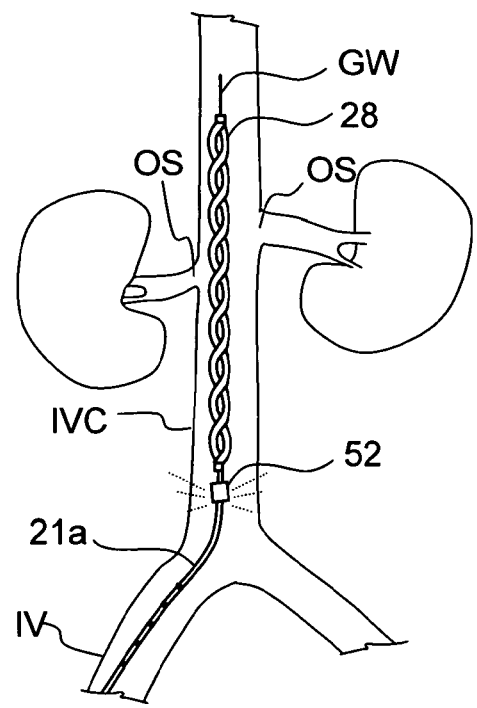

FIG. 4B is a diagram of the inferior vena cava and iliac bifurcation of a human subject with a heat exchange catheter of the present invention inserted therein, such heat exchange catheter having an optional energy emitting device (e.g., sonic or ultrasonic) located just proximal to the heat exchange balloon, such energy emitting device being useable to determine the approximate diameter of the blood vessel in which it is positioned and to thereby determine when substantially the entire heat exchange balloon has been advanced through the iliac vein and into the inferior vena cava.

Figure 4C:
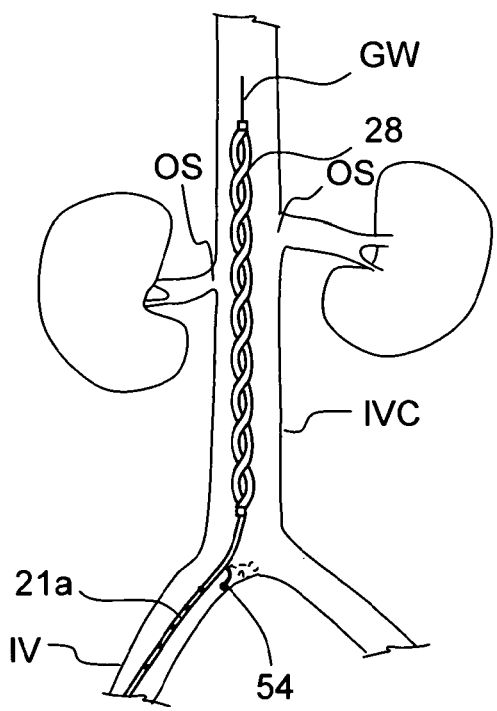

FIG. 4C is a diagram of the inferior vena cava and iliac bifurcation of a human subject with a heat exchange catheter of the present invention inserted therein, such heat exchange catheter having an optional probe member positioned just proximal to the heat exchange balloon, such probe member being constructed to contact or "feel" the adjacent wall of the blood vessel to detect changes in the diameter, size or anatomy of the surrounding blood vessel and to thereby determine when substantially the entire heat exchange balloon has been advanced through the iliac vein and into the inferior vena cava.

Figure 4D:
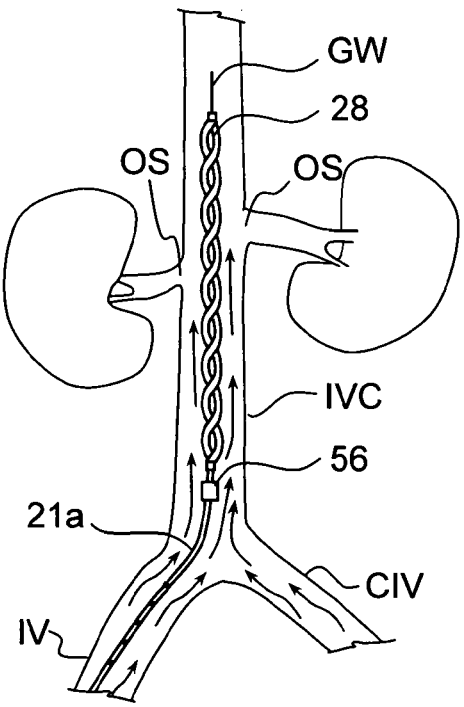

FIG. 4D is a diagram of the inferior vena cava and iliac bifurcation of a human subject with a heat exchange catheter of the present invention inserted therein, such heat exchange catheter having an optional flowmeter positioned just proximal to the heat exchange balloon, such flowmeter being operative to detect changes in the flowrate and/or flow patterns of blood and to thereby determine when substantially the entire heat exchange balloon has been advanced through the iliac vein and into the inferior vena cava.

FIG. 5A is a cross sectional view of a tri-lobed heat exchange balloon of the prior art in its expanded configuration.

FIG. 5B is cross sectional view of a tri-lobed heat exchange balloon of the present invention in its expanded configuration.

FIGS. 5B', 5B" and 5B'" show examples of varying degrees of twisting that may be induced in the tri-lobed heat exchange balloons of the present invention.

Figure 6:
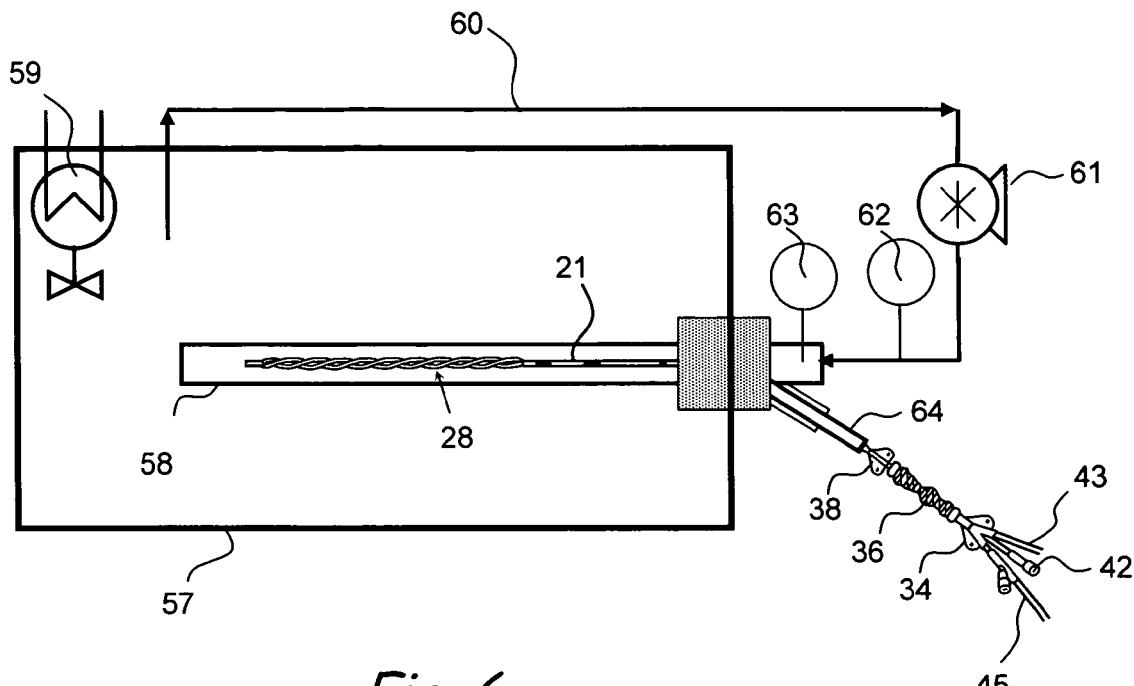

FIG. 6 is an in vitro water bath flow model for testing the cooling (or warming) power of the endovascular heat exchange catheters of the prior art and present invention.

Figure 7:
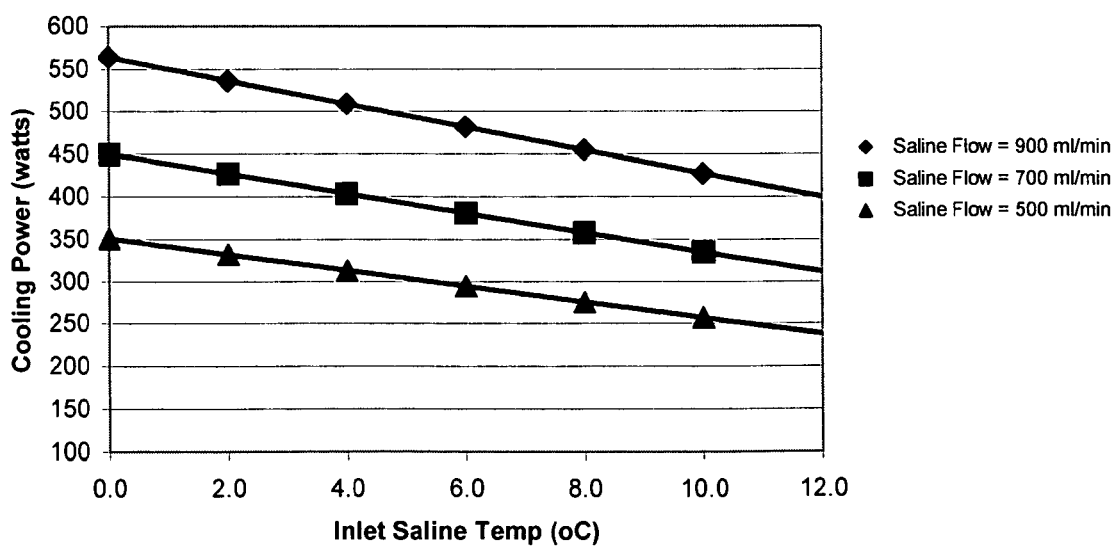

FIG. 7 is a graph showing the effects of incoming thermal exchange fluid temperature and flowrate on cooling power in endovascular heat exchange catheters of the present invention.

Figure 8:
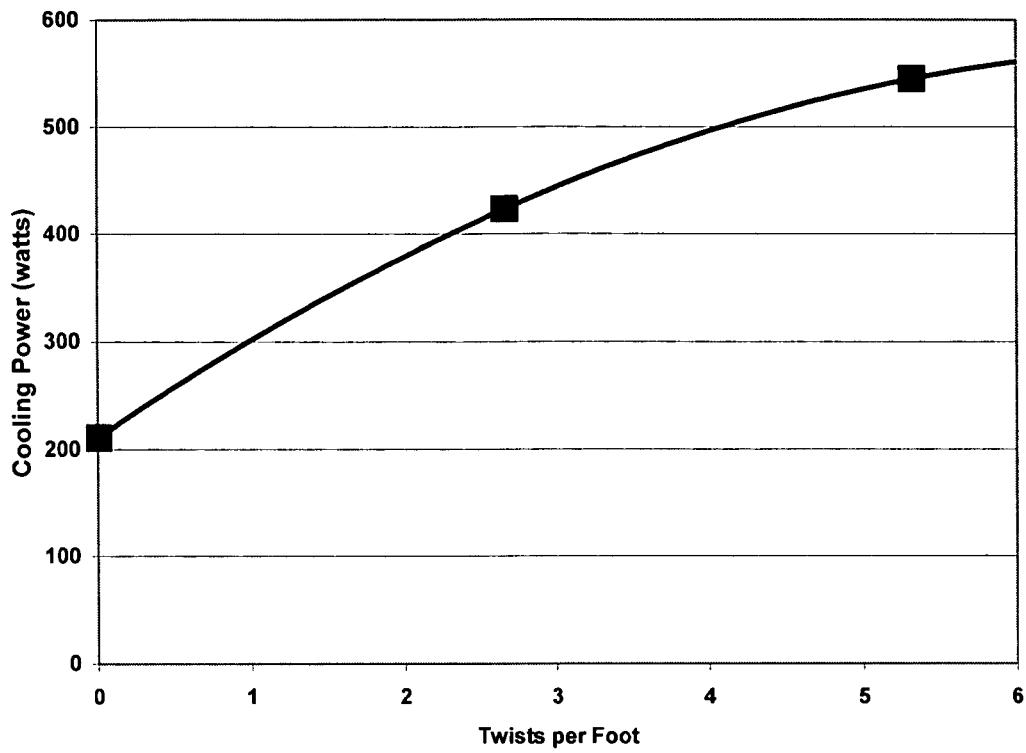

FIG. 8 is a graph showing the effect of the tightness of balloon twisting on heat exchange power in an endovascular heat exchange catheter of the present invention having a tri-lobed heat exchange balloon.

Figure 9:
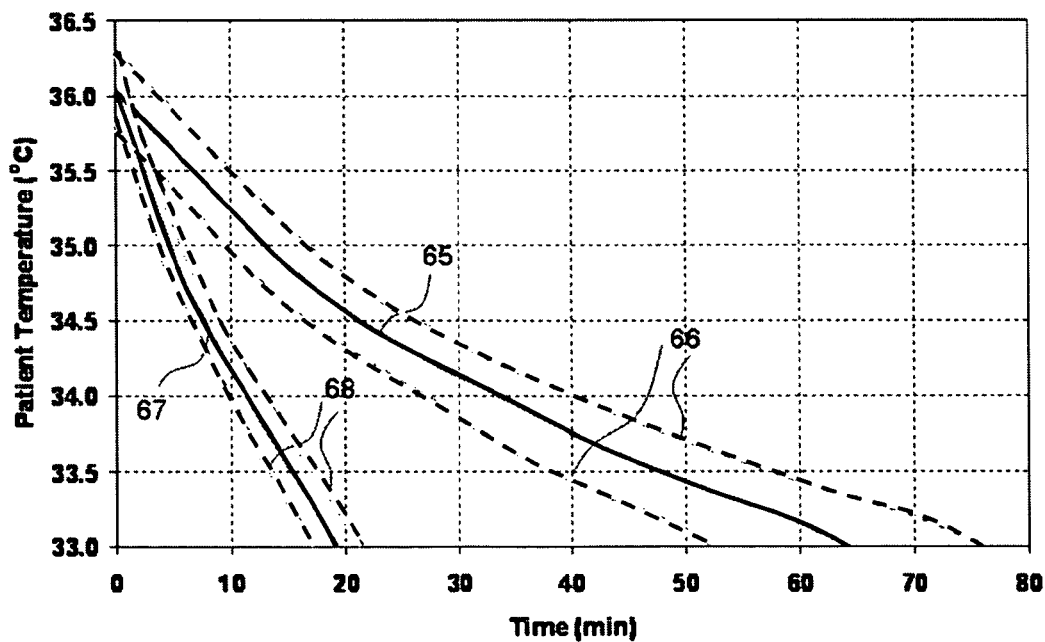

FIG. 9 is a graph showing cooling performance of the endovascular heat exchange catheters of the prior art and present invention.

Figure 10:
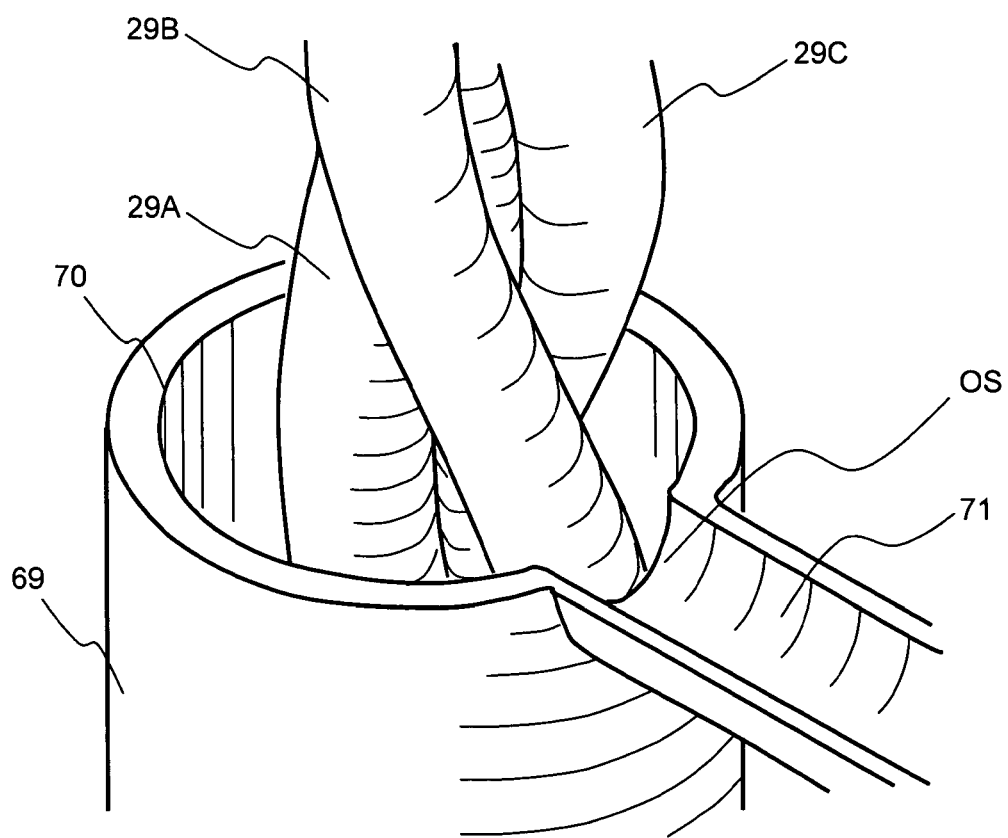

FIG. 10 is a drawing of a heat exchange catheter of the present invention positioned in an inferior vena cava (IVC) that has a luminal diameter of 21 mm such that a lobe of the catheter's heat exchange balloon maximally obstructs a 7 mm diameter branch vessel.

DETAILED DESCRIPTION

The following detailed description, the accompanying drawings and the above-set-forth brief descriptions of the drawings are intended to describe some, but not necessarily all, examples or embodiments of the invention. The contents of this detailed description, the accompanying drawings and the above-set-forth brief descriptions of the drawings do not limit the scope of the invention, or the scope of the following claims, in any way.

Figures 1A, 1B, 1C:
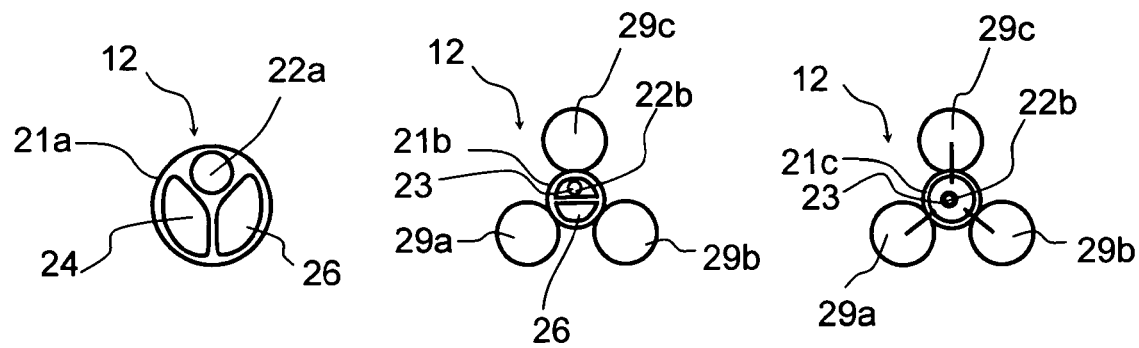
FIG. 1A is a cross-section through line 1A-1A of FIG. 1.
FIG. 1B is a cross-section through line 1B-1B of FIG. 1.
FIG. 1C is a cross-section through line 1C-1C of FIG. 1.
Figure 1:
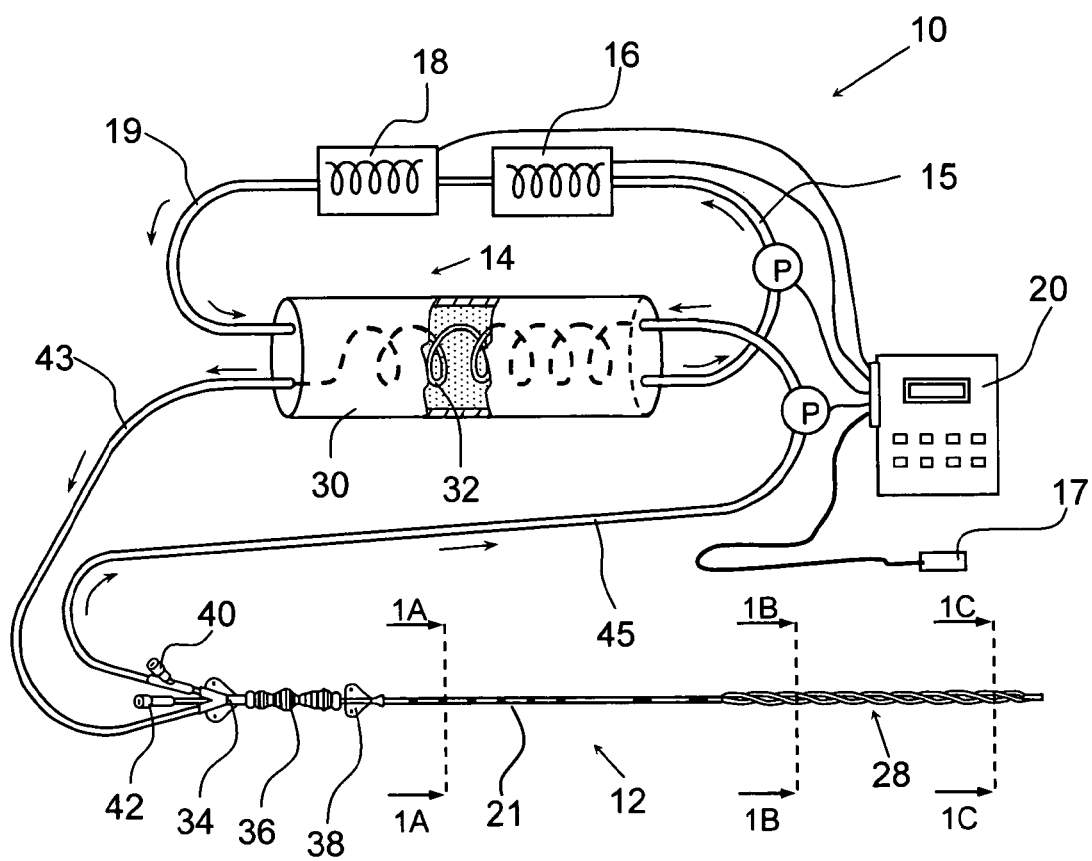
FIG. 1 is a diagram of an endovascular heat exchange system of the present invention.

FIG. 1 is a diagrammatic example of a heat exchange catheter system 10 of the present invention. In this example, the heat exchange catheter system 10 generally comprises a) a heat exchange catheter 12, b) an extracorporeal heat exchanger 14, c) a cooler 16 and/or heater 18, d) a body temperature measuring apparatus 17 and e) a programmable controller 20. In some instances, a cooler 16 and heater 18 may be combined or integrated into a single apparatus that alternately heats and cools (e.g., a thermoelectric cooler/heater) while in other instances a separate cooler 16 (e.g., a refrigerator, condenser, thermoelectric cooler, mass of cold matter, etc) and/or separate heater (e.g., a resistance heater, thermoelectric heater, mass of warm matter, etc.) may be used.

The heat exchange catheter 12 comprises an elongate catheter body 21 having an intracorporeal heat exchanger 28 mounted thereon. As shown in the cross section of FIG. 1A, a proximal portion of the catheter comprises a proximal shaft 21a having a first thermal exchange fluid lumen 24, a second thermal exchange fluid lumen 26 and a working lumen 22a. At or near the distal end of the proximal shaft 21a the first thermal exchange fluid lumen 24 terminates and communicates through openings into three generally cylindrical balloon lobes 29a, 29b and 29c such that thermal exchange fluid may flow out of proximal portions of the balloon lobes 29a, 29b and 29c and into the first thermal exchange fluid lumen 24. Thus, in this example, the first thermal exchange fluid lumen 24 carries outflow of the thermal exchange fluid from the intracorporeal heat exchanger 28 back toward the extracorporeal heat exchanger.

As seen in the cross section of FIG. 1B, balloon lobes 29a, 29b and 29c are twisted, wound or otherwise helically disposed about a mid-portion 21b of the catheter shaft. In this example, the mid-portion 21b of the catheter shaft comprises a continuation or extension of the second thermal exchange fluid lumen 26 along with a smaller tube 23 having a lumen 22b that is connected to and forms a continuation or extension of the proximal working lumen 22a. The balloon lobes 29a, 29b and 29c and the second thermal exchange fluid lumen 26 terminate at the distal end of the mid-portion 21*b* of the catheter shaft. Also at or near the distal end of the mid-portion 21*b* of the catheter shaft the second thermal exchange fluid lumen 26 terminates and communicates through openings into three generally cylindrical balloon lobes 29*a*, 29*b* and 29*c* such that thermal exchange fluid may flow from the second thermal exchange fluid lumen 26 and into distal portions of the balloon lobes 29*a*, 29*b* and 29*c*. Thus, in this example, the second thermal exchange fluid lumen 26 carries inflow of the thermal exchange fluid to the intracorporeal heat exchanger 28. The attachment of the balloon lobes to the catheter may be accomplished in any appropriate manner to accomplish the circulation of heat exchange fluid described here. One such method is described in detail in U.S. Pat. No. 6,610,083 (Keller, et al.), which patent is expressly incorporated herein by reference.

As shown in the cross section of FIG. 1C, a distal portion 21*c* of the catheter shaft extends beyond the distal ends of the balloon lobes 29*a*, 29*b* and 29*c*. Tube 23 having working lumen 22*b* continues through this distal portion 21*c* of the catheter shaft and its lumen 22*b* opens through an aperture in the distal tip of the catheter 12. Thus, in this manner, the working lumen 22*a* of the proximal catheter shaft 21*a* and working lumen 22*b* of the mid-portion and distal catheter shafts 21*b*, 21*c* combine to form a continuous working lumen that extends through the shaft 21 of the heat exchange catheter 12. In some embodiments, a working lumen that runs less than the entire length of the catheter shaft 21 may be provided to facilitate rapid exchange of guidewires and/or catheters. As those of skill in the art will appreciate, such working lumen 22*a*, 22*b* may facilitate advancement of the catheter 12 over a guidewire and/or to facilitate infusion of fluids (e.g., saline solution, therapeutic or diagnostic substances, radiographic contrast medium, aqueous oxygen, etc.) and/or to facilitate introduction of another catheter or apparatus into the subject's body. One example of another apparatus that may be advanced through the working lumen 22*a*, 22*b* is an endovascular embodiment of the body temperature measuring apparatus 17 (e.g., a catheter or wire having a temperature sensor that is advanceable out of the distal tip of the catheter 12 or shaft 21 and useable for sensing the temperature of the subject's flowing blood). One example of an endovascular embodiment of the body temperature measuring apparatus 17 that may be advanced through working lumen 22*a*, 22*b* is the Reprieve® endovascular temperature probe manufactured by Radiant Medical, Inc., Redwood City, Calif.

As shown in FIG. 1, the proximal end of the catheter shaft 21 may be provided with a generally tubular, flexible sterility barrier 36 disposed between proximal hub 34 and distal hub 38. The catheter shaft 21 may be slideably advanced and retracted through the distal hub 38 while the proximal hub 34 is affixed in a substantially stationary manner to the catheter shaft 21. The distal hub 38 may be affixed to the subject's skin by sutures, adhesive or other means, at a location immediately adjacent to the location where the catheter shaft 21 enters percutaneously into the subject's body. At the time of initial insertion, the catheter shaft 21 is advanced into the subject's body to a desired initial position. In some applications, the specific positioning of the intracorporeal heat exchanger 28 within the body may affect the efficiency and rapidity with which the intracorporeal heat exchanger 28 heats or cools the subject's body. In this regard, some heat exchange catheters 12 of the present invention may include optional elements useable to facilitate positioning of the entire intracorporeal heat exchanger 28 at a desired position within the body (e.g., within the inferior vena cava). Examples of such optional elements are shown in FIGS. 4A-4D and described fully herebelow. After the catheter shaft 21 has been advanced to its desired initial position, the proximal and distal hubs are affixed to the subject's skin such that the sterility barrier 36 encases and maintains sterility of the exteriorized portion of the catheter shaft 21. At a later time if it is desired to adjust the position of the catheter 12, the proximal hub 34 may be detached from the subject's body and the catheter shaft may be further advanced or retracted, as needed, through the distal hub 38. When the desired repositioning of the catheter 12 has been achieved, the proximal hub 34 may one again be affixed to the subject's body and the sterility barrier 36 will continue to shield the exteriorized portion of the catheter shaft 21 from contamination. Further details and examples of this arrangement as well as other valving systems and other elements that may be incorporated into the proximal end of the catheter device 12 are described in U.S. Pat. No. 6,887,263 (Bleam et al.) which is expressly incorporated herein by reference.

A valved port 42, such as tube having a Tuohy-Borst valve, is attached to the proximal end of the proximal working lumen 22*a* to facilitate advancement of a guidewire, infusion of fluids (e.g., saline solution, therapeutic or diagnostic substances, radiographic contrast medium, etc.) or introduction of other catheter or apparatus into the subject's body through working lumen 22*a*, 22*b*.

A second valved port 40, such as a such as Y tube having a stopcock on one arm thereof, is attached to the proximal end of the first thermal exchange lumen 24 to facilitate venting or purging or air or unwanted fluid from the system during the initial filling of the system with thermal exchange fluid.

With reference to FIG. 1, the extracorporeal heat exchanger 14 comprises a shell 30 having an inner tube 32 extending therethrough. Outflow tube 45 connects the first thermal exchange lumen 24 to the inlet of the inner tube 32 and inflow tube 43 connects the outlet of the inner tube 32 to the second thermal exchange lumen 26.

Thermal exchange fluid is thus pumped from the inner tube 32 of the extracorporeal heat exchanger 14, through the second (inflow) thermal exchange lumen 26, into the distal portions of balloon lobes 29*a*, 29*b*, 29*c*, through the balloon lobes 29*a*, 29*b*, 29*c* in the proximal direction, into the first (outflow) thermal exchange lumen 24, through tube 45 and back into the inner tube 32 of the extracorporeal heat exchanger 14. Tube 15 connects an outlet from the shell 30 of extracorporeal heat exchanger 14 to cooler 16 and/or heater 18. Tube 19 connects the cooler 16 and/or heater 18 to an inlet of the shell 30 of extracorporeal heat exchanger 14. Thus, heated or cooled fluid (e.g., a glycol such as propylene glycol or other suitable thermal exchange fluid) circulates from the cooler 16 and/or heater 18, through tube 19, through the shell 30 of extracorporeal heat exchanger 14, through tube 15 and again through cooler 16 and/or heater 18. The operator inputs into the controller 20 a target body temperature. The controller 20 is in communication with the body temperature measuring apparatus 17 and receives signals indicative of the temperature of all or a portion of the subject's body. The controller 20 controls one or more of: a) the operation of the cooler 16 and/or heater 18, b) the flowrate of the heated or cooled fluid through the extracorporeal heat exchanger, c) the flowrate of thermal exchange fluid through the extracorporeal heat exchanger 14, and/or the flowrate of thermal exchange fluid through the intracorporeal heat exchanger 28, thereby causing the subject's body to be cooled or warmed to the desired target body temperature and maintaining such target body temperature for a desired period of time.

During initial insertion of the catheter 12, the balloon lobes 29a, 29b, 29c are deflated and collapsed to a low profile that is the same or only slightly larger in diameter than the adjacent catheter shaft 21. After the catheter 12 has been inserted into the subject's vasculature, the thermal exchange fluid is allowed to flow into the balloon lobes 29a, 29b, 29c, thereby causing the lobes to inflate or expand. (The lobes "inflate" in the sense that they become substantially filled with liquid and take on their full expanded size and shape. However, it is to be appreciated that in at least some embodiments the lobes may be non-compliant or semi-compliant (e.g., polyethylene theaphthalate (PET) or Nylon) balloons with a wall thickness of between 0.00040 inches and 0.00065 inches.) Thus, the intracorporeal heat exchanger 28 has a balloon with a first circumscribed diameter D1 when the balloon lobes 29a, 29b, 29c are empty and collapsed and a second circumscribed diameter D2 when the balloon lobes 29a, 29b, 29c are fully filled and inflated. It is desirable that the first circumscribed diameter D1 be small enough to allow the catheter 12 to be inserted through a vascular introducer of a desired size. Additionally, the efficiency or rapidity of heat exchange is directly affected by a number of factors, one of which is the blood-contacting surface area of the inflated balloon lobes 29a, 29b, 29c. Essentially, the greater the blood contacting surface area of the balloon lobes 29a, 29b, 29c, the greater the efficiency and rapidity of blood cooling or warming. However, the second circumscribed diameter D2 should typically be smaller than the diameter of the blood vessel lumen in which the intracorporeal heat exchanger 28 is positioned so and not to substantially obstruct the flow of blood through that blood vessel lumen. An advantage of the multi-lobed balloon 28 of the present invention over intravascular heat exchange balloons of the prior art is that the heat exchange balloon 28 of the present invention may be expanded within a vessel to a second circumscribed diameter D2 that near or equal to the luminal diameter of the vessel but the resultant blockage of cross-sectional area of the vessel's lumen is limited to approximately 50% due to the sizing of the lobes 29a, 29b, 29c and the presence of flow path(s) between the lobes 29a, 29b, 29c. This is comparable with in vivo testing of the Greenfield IVC filter, a conical shaped screen type device where blockages equivalent to 64% of cross-sectional area have occurred without development of a pressure gradient across the filter.

In applications where the catheter is to be inserted into the femoral vein of an adult human being and advanced to a position within the inferior vena cava, use of a vascular introducer no larger than 12 to 14 French will be desired. Thus, in embodiments intended for femoral insertion, it is preferable that the first circumscribed diameter D1 be less than about 4.7 mm, or in some cases less than about 4.5 mm, or otherwise sized to fit through a 14 French or smaller vascular introducer. The lumen of the inferior vena cava of an adult human typically has an average diameter of 20-22 mm. Thus, to maximize efficiency and/or rapidity of cooling or warming while not substantially obstructing blood flow, in embodiments intended for femoral insertion and advancement of the intracorporeal heat exchanger 28 into the inferior vena cava of an adult, it is preferable that the second circumscribed diameter D2 be greater than about 14 mm. Accordingly, in such embodiments of the catheter 12, the second circumscribed diameter D2 will desirably be at least about 3 times greater than the first circumscribed diameter D1.

Additionally, to provide sufficient efficiency and/or rapidity of thermal exchange to be useable in certain therapeutic applications (e.g., treatment of myocardial infarction) the cross sectional perimeter of the intracorporeal heat exchanger may be sized to maximize the blood-contacting heat exchange surface area. In this regard, in embodiments intended for femoral insertion and advancement of the intracorporeal heat exchanger 28 into the inferior vena cava of an adult, it is preferable that the cross sectional perimeter of the intracorporeal heat exchanger 28 be in the range of about 2.0 inches to about 2.5 inches and the length be in the range of 20 to 25 cm for average adults. Heat exchange catheters of different sizes may be provided for use in individuals of varying body size or anatomy. For example, the catheter 12 shown in FIGS. 1-1c may be provided with heat exchangers 28 having length of 22.5 cm and cross sectional perimeters of 1.5 inch, 2.0 inch and 2.5 inch and/or other sizes for pediatric applications or applications where the heat exchanger 28 is to be positioned in a blood vessel other than the inferior vena cava.

Figure 2:
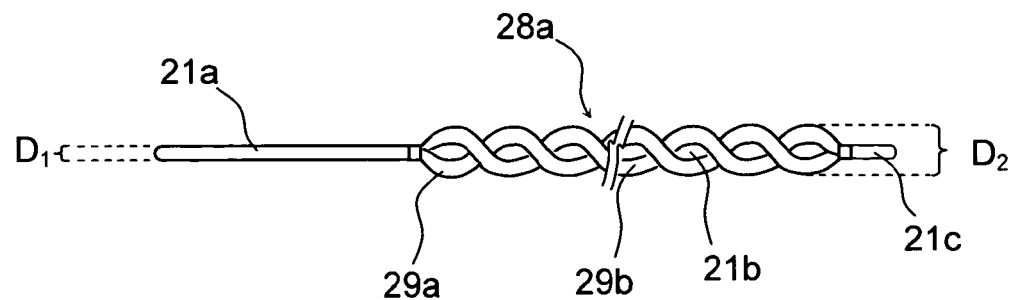
FIG. 2 is a side view of a distal portion of an endovascular heat exchange catheter device of the present invention with its heat exchange balloon deployed in a fully expanded state.
Figure 3:
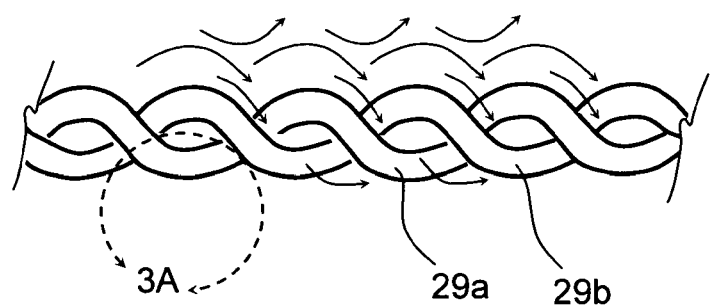
FIG. 3 is a side view of a portion of the heat exchange catheter device of FIG. 2A with arrows showing an example of the manner in which blood or other body fluid may flow adjacent to the heat exchange balloon.
Figure 3:
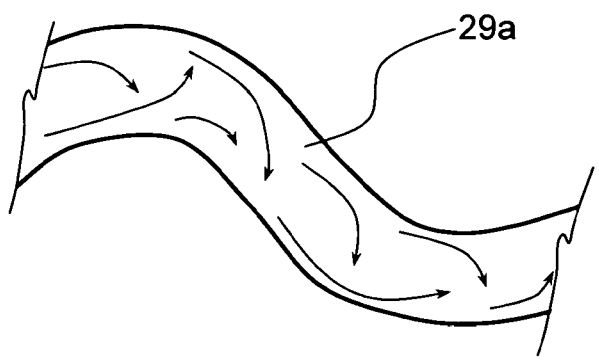
Figure 5:
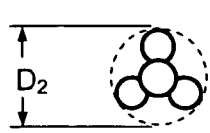
Figure 5:
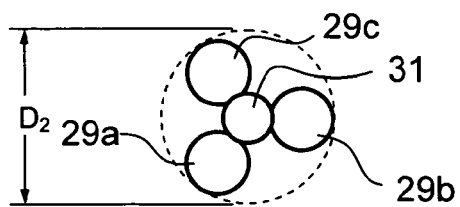
Figure 5:
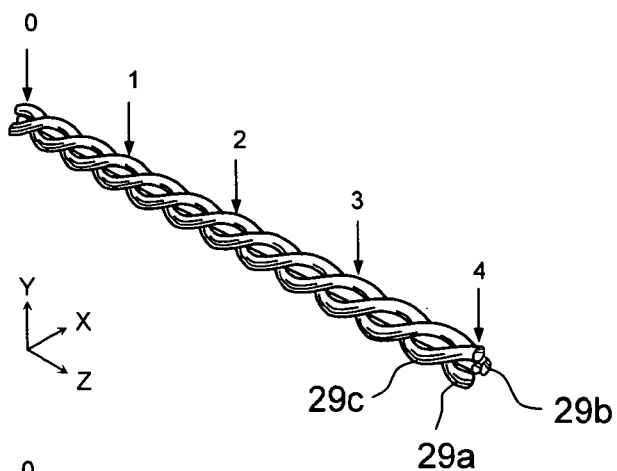
Figure 5:
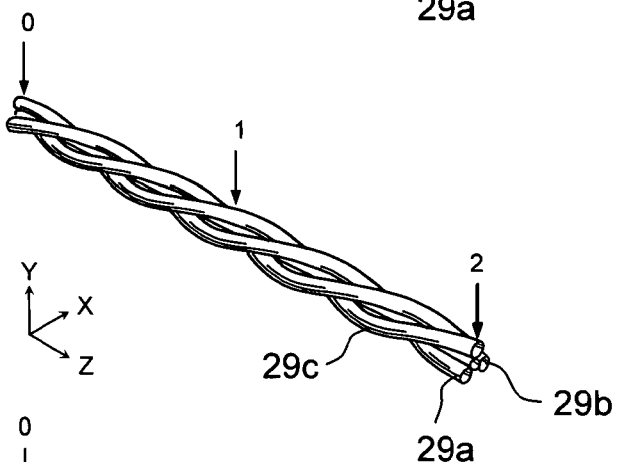
Figure 5:
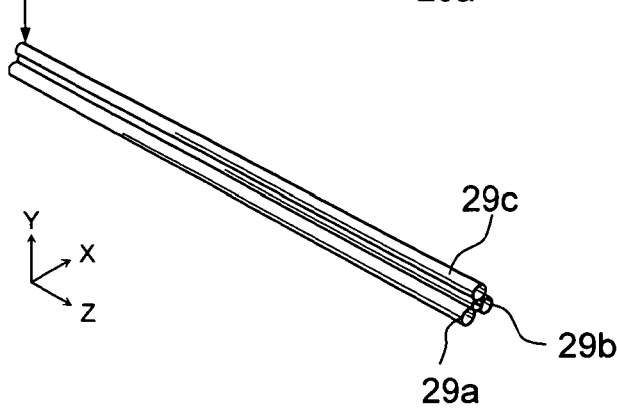

Another factor that, in at least some applications, affects the efficiency and/or rapidity of heating or cooling of the subject's body is the shape or configuration of the balloon lobes 29a, 29b, 29c. As illustrated in the schematic showings of FIGS. 2-3A, the balloon lobes 29a, 29b, 29c may be disposed in a helical configuration that will cause mixing or tumbling rather than smooth flow of blood as it flow past the heat exchanger 28 (see FIG. 3) and will also cause mixing or tumbling of thermal exchange fluid flowing through each balloon lobe 29a, 29b, 29c (see FIG. 3A). Thus, as shown in FIGS. 5B'-5B''' and described in the example calculations set forth below, the number of twists or convolutions of each helical balloon lobe 29a, 29b, 29c may be optimized, along with other factors such as perimeter surface area, to provide for a desired efficiency or rapidity of body warming or cooling. An advantageous configuration has been found to be a minimum of 4 twists per foot, where twists are counted in the convention illustrated in FIG. 5, and refer to the helical rotations about a central axis. In the heat exchange balloon 28 described herein, the helical lobes 29a, 29b, 29c are helically disposed about a central lobe 31 that is generally in the configuration of a linear cylinder, although this central lobe 31 may be may be "twisted" during manufacture resulting in structural tensions in the walls of that lobe 31, the term "twists per foot" as used herein refers only to the number of rotations of each outer lobe 29a, 29b, 29c around the central lobe 31 or other longitudinal axis and not the molecular or structural tensioning of the walls of the central lobe 31.

Motion of the heat exchange balloon further enhances heat exchange. Pulsatile flow of the heat exchange fluid, when using a heat exchange balloon such as the helically twisted lobes attached to a generally linear central spine can result in particularly advantageous motion that enhances heat exchange. Additional twisting of the lobes of heat exchanger 28 is possible prior to attachment to shaft 21 to further enhance the movement of the balloon due to the torque induced from the fluid momentum. With pulsatile blood flow and pulsatile balloon motion combined, the tumbling effect produced in the blood and in the heat exchange fluid is particularly effective in enhancing heat exchange.

Another factor that, in at least some applications, affects the efficiency and/or rapidity of heating or cooling of the subject's body is the positioning of the intracorporeal heat exchanger 28 within the subject's body. For example, in applications where the heat exchange catheter 12 is to be inserted into a femoral vein and advanced through the iliac vein to a position were the intracorporeal heat exchanger 28 is positioned within the inferior vena cava, a significant impairment of thermal exchange efficiency may occur if the entire intracorporeal heat exchanger 28 is not positioned within the inferior vena cava. For example, if the catheter 12 is not advanced far enough into the body, a proximal portion of the intracorporeal heat exchanger 28 may remain within the iliac vein rather than the inferior vena cava. Because the volume of blood flowing though each iliac vein is approximately 50% of that flowing through the vena cava, the portion of the intracorporeal heat exchanger 28 that remains in the iliac vein will be exposed to less blood flow and will thus heat or cool less blood than if it were properly positioned in the inferior vena cava. Radiopaque markings may be provided at one or both ends of the intracorporeal heat exchanger so that the position of the intracorporeal heat exchanger 28 may be determined by X ray or other radiographing imaging technique. However, in many emergency departments or other clinical settings, the time required to obtain such x ray or other radiographic image may be longer than optimal. Valuable heating or cooling time may be lost before it is determined by x ray or radiographic imaging that the catheter 12 is not optimally positioned. Thus, to facilitate the desired positioning of the intracorporeal heat exchanger 28 without requiring an x ray or other radiographic image, heat exchange catheters 12 of the present invention may optionally incorporate one or more elements (e.g., markings, indicators, devices, apparatus, etc.) that indicate when the intracorporeal heat exchanger 28 has reached a desired position within the subject's body. Some non-limiting examples of such elements are shown in FIGS. 4A-4D.

FIG. 4A shown an embodiment where the proximal catheter shaft 21*a* has a series of spaced apart markings 50 that may be used to gage when a sufficient length of the catheter 12 has been advanced into the subject. Different markings 50 may correspond to subjects of different body size or anatomy. For example, an article or device for correlating a specific distance marking 50 to a patient of a specific body size or anatomy (e.g., a nomogram, pre-programmed electronic or manual calculator, look-up table, index, etc.) may be provided to the operator along with the catheter 12. The clinician may use available data on the subject's body size and/or anatomy to determine which distance marking 50 should apply for that particular subject. The marks 50 may be distinguishable from one another by shape, color, etc. After determining which mark 50 should apply for the particular subject, the operator may then advance the catheter 12 into the subject's body until the selected mark 50 is immediately adjacent to the percutaneous insertion point into the femoral vein, thereby indicating a likelihood that the entire intracorporeal heat exchanger 28 has been advanced through the iliac vein IV and into the inferior vena cava IVC.

FIG. 4B shows an embodiment where a vessel diameter sensor 52, such as an intravascular ultrasound (IVUS) device, is positioned on the proximal catheter shaft 21*a* proximal to heat exchanger 28. The catheter 12 may be advanced until the vessel diameter sensor 56 senses (and provides a perceptible signal to the operator) that it has passed from the smaller diameter iliac vein IV into the larger diameter inferior vena cava IVC.

FIG. 4C shows an embodiment where a vessel wall contacting probe 54, such as a spring loaded switch arm, extends from the proximal catheter shaft 21*a* and contacts the adjacent vessel wall as the catheter is advanced through the iliac vein IV. As the vessel wall contacting probe 54 passes from the smaller diameter iliac vein IV into the larger diameter inferior vena cava IVC, the vessel wall contacting probe 54 will extend or spring to a less constrained or non-constrained position and will provide a signal (e.g., an alarm, light, audible signal, sensory change noticeable to the touch of a skilled operator, etc) to the operator thereby indicating that the entire intracorporeal heat exchanger 28 has been advanced into the inferior vena cava IVC as intended.

FIG. 4D shows an embodiment where a flow sensor 56 is positioned on the proximal catheter shaft 21*a* proximal to heat exchanger 28. The catheter 12 may be advanced until the flow sensor 56 senses incoming blood flow from the contralateral iliac vein IV or other change in the blood flow dynamics indicating that the flow sensor 56 has passed form the iliac vein IV into the inferior vena cava IVC. The system then provides a signal (e.g., an alarm, light, audible signal, etc) indicating that the flow sensor 56 has advanced from the iliac vein IV into the inferior vena cava IVC, thereby ensuring that the entire intracorporeal heat exchanger 28 has been advanced into the inferior vena cava IVC.

FIGS. 5A and 5B show cross sectional views of a tri-lobed heat exchange balloon of the prior art and of the present invention, respectively, in their expanded configurations. FIGS. 5B', 5B" and 5B''' show examples of varying degrees of twisting that may be induced in the tri-lobed heat exchange balloons of the present invention to increase heat exchange.

In one study, it was observed that conscious patients at risk for radiocontrast nephropathy could be cooled with a prior art heat exchange balloon at the average rate of 3 degrees in 64 minutes. In the total of 14 patients, however, the range was 32 to 110 minutes. Because of the dependence of cooling rate on catheter position and non-catheter related factors such as the blood velocity (which itself is dependent upon the vessel size, and the cardiac output), blood viscosity, location and accuracy of the temperature measurement (intravascular, nasoesophageal, bladder, tympanic, etc), and heat inputs to the body from variable sources such as heating blankets, shivering, or base metabolism, it is best to characterize the heat exchange capability of a given design in terms of steady state heat transfer in a simplified or "standard" in vitro model where these variables can be eliminated or held constant.

FIG. 6 illustrates an example of an in vitro water tank model suitable for this purpose. Tank 57 is fitted with a rigid tube 58 of known diameter. Circulating tank heater 59 is used to maintain the tank volume (and liquid within the tube 58) at the desired temperature. Water pump 61 withdraws water from tank 57 and returns it through tube 58 in a closed loop. Flow meter 62 and temperature sensor 63 are used to verify outputs or control water pump 61 and circulating heater 59, respectively. Tank 57 is adapted with introducer 64 to allow placement of heat exchange balloon 28 within tube 58. When the heat exchange system is in use and the conditions are stable, the amount of heat transfer in the system can be calculated by either from a heat balance in the water pump circuit, or preferably from the difference in incoming and outgoing thermal exchange fluid temperature in the heat exchange catheter itself by methods known to those experienced in the art.

With tube 58 at 22 mm ID, water pump 61 set to 2.5 liters per minute and the inlet temperature 63 controlled to 37.0 degrees Celsius, the prior art catheter with a 25 cm balloon length and circumscribed diameter of 9 mm (FIG. 5A) was capable of 180-200 watts of steady state cooling.

The test model illustrated in FIG. 6 and described above was used to characterize and optimize the heat exchange catheter of the present invention. FIG. 7 is an exemplary graph showing the effects of incoming thermal exchange fluid temperature and flow rate on cooling power of a 25 cm balloon length and 15.2 mm circumscribed diameter embodiment of FIG. 5B. FIG. 8 is a graph showing the effect of the tightness of balloon twisting on heat exchange power in an endovascular heat exchange catheter of the present invention. In an example, the catheter body, fluid cooling apparatus and heat exchange balloon are sized, configured and constructed to render the system capable of delivering at least about 400 watts of cooling power.

Using both computational fluid dynamics and experimental verification with the "standard" water tank model shown in FIG. 6, an empirical working model of the cooling power of the heat exchange system may be determined by Equation I as follows:

$$\text{Standard Cooling Power (watts)} = (45.9 + 176.57 * P - 0.105 * Q + 0.582 * T + 0.113 * P * Q - 6.486 * P * T) * (L/25.0) * (-0.1631 * W + 1.0816) * (-0.0013 * S^2 + 0.0595 * S + 0.387)$$

wherein, P is the heat exchange catheter 28 cross-sectional perimeter
in inches, Q is the flow rate of thermal exchange fluid in ml/min, T is the temperature of the thermal exchange fluid in degrees Celsius (° C.) as it enters the second lumen 26, L is the length of the heat exchange catheter 28 in cm, W is the thickness of the heat exchange catheter 28 wall in mils and S is the total number of twists of the balloon lobes per foot of the balloon.

A preferred embodiment of the present invention having on average 450 watts of cooling in the model represented in FIG. 6 and discussed above was studied in the same clinical trial as the prior art and cooled patients at the average rate of 3 degrees in 19 minutes. In the total of 19 patients, the range was 11 to 33 minutes. The data for this study is illustrated in FIG. 9. Curve 65 represents the prior art with 95% confidence bands given by curves 66. Curve 67 represents the average for the present invention with 95% confidence bands 68.

The heat exchanger 28 may, in some applications, be positioned adjacent to the ostium OS of an adjacent branch vessel. For example, in the showings of FIGS. 4A-4D, the heat exchanger 28 is positioned within the inferior vena cava IVC adjacent to the ostia OS of the renal veins RV. Also, FIG. 10 is a diagram showing the heat exchanger 28 positioned within a blood vessel 69 adjacent to the ostium OS of a branch vessel 71. While inflated and in routine operation, the circumscribed outer diameter of the heat exchanger 28 may be sufficiently large to cause the heat exchanger 28 to be close to or in contact with one or more ostia OS of branch vessels. In an adult human patient, the radial position of the heat exchanger 28 within a blood vessel is not expected to be static. Rather, dynamic blood flow through the vessel 69 as well as other physiologic movement suspends the catheter in the vessel and keeps it from resting in a single position against any ostium OS for any clinically significant length of time. Consequently, in most cases the lobes 29a, 29b, 29c of the heat exchanger 28 would rest across the ostium OS of a branch vessel 71 only transiently. In the preferred embodiment of placement of the catheter within the IVC, the significant flow through the renal and hepatic veins would likely displace an object lying over their junctions with the IVC.

In a worst-case scenario where patient condition renders the vessel 69 smaller than the circumscribed diameter D2 of the inflated heat exchange balloon 28 or where the vessel 69 is less dynamic than normally expected, the heat exchange balloon 28 could rest over the ostium of the incoming vein 71 such that a lobe 29B would cross the ostium. This situation does not, however, present an unacceptable risk due to the advantageous configuration provided by the multiple twisted lobes of the present invention. The average renal vein has been reported as between 7 and 10 mm in diameter. Similarly, the average size of the hepatic vein ostia has been reported as 15 mm for the right hepatic vein and 13 mm for the left hepatic vein, while the reported average hepatic vein diameter is 7.5 mm to 10.0 mm (left). By comparison, the maximum diameter of a single lobe 29 in the present invention is 6.5 mm (FIG. 5B). In the 3-dimensional representation of FIG. 10, it is evident that the obstruction is partial and allows blood flow from the tributary vessel. Thus, the combination of lobe 29a, 29b, 29c diameters that are less than the diameters of the ostia of the branch vessels encountered and the provision of helical blood flow channels (e.g., grooves or indentations) between the lobes 29a, 29b, 29c, serve to substantially deter any clinically significant obstruction of the ostium of a branch vessel from which blood flows into or out of the blood vessel in which the heat exchanger 28 is positioned.

The invention has been described hereabove with reference to certain examples or embodiments of the invention. No attempt has been made to exhaustively describe all possible embodiments and examples of the invention. Indeed, various additions, deletions, alterations and modifications may be made to the above described examples and embodiments without departing from the intended spirit and scope of the invention.

For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example un-novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A heat exchange catheter configured for connection to an extracorporeal device having a cooler which comprises a heat exchanger which uses cold heat exchange fluid from the cooler to cool a thermal exchange fluid that circulates through the heat exchange catheter, said heat exchange catheter comprising:
   a flexible catheter shaft having a proximal end, a distal end, an inflow lumen, an outflow lumen; and
   a heat exchange balloon connected to the inflow and outflow lumens such that, when the catheter is connected to said fluid cooling apparatus, thermal exchange fluid will circulate from the extracorporeal heat exchanger, through the inflow lumen, through the balloon, through the outflow lumen and back to the extracorporeal heat exchanger;
   the heat exchange balloon being collapsible to a collapsed configuration such that a distal portion of the catheter shaft, inclusive of the heat exchange balloon in said collapsed configuration, is insertable into a human subject's vasculature through a tubular introducer, said heat exchange balloon being thereafter expandable, by circulation of thermal exchange fluid therethrough, to an expanded configuration that has at least 125 cm² of blood contacting surface area;

the heat exchange balloon, when connected to said extracorporeal heat exchanger and positioned in a fluid having a temperature of 37 degrees C. while in said expanded configuration with cooled thermal exchange fluid being circulated therethrough, being capable of delivering a least 400 Watts of cooling power.

2. A heat exchange catheter according to claim 1 wherein the heat exchange balloon has a wall thickness of less than 0.01651 mm.

3. A catheter according to claim 1 wherein the heat exchange balloon comprises tubular balloon lobes twisted in a substantially helical configuration about a central axis.

4. A catheter according to claim 3 wherein the tubular balloon lobes have at least four twists per linear 304.8 mm.

5. A catheter according to claim 4 wherein the heat exchange balloon further comprises a central lobe around which the tubular balloon lobes are positioned, said central lobe being configured such that thermal exchange fluid will flow through the central lobe in a first direction, then enter the tubular balloon outer lobes, and then flow through the tubular balloon outer lobes in a second direction that is generally opposite said first direction.

6. A catheter according to claim 1 wherein the heat exchange balloon has a cross sectional perimeter between 55.88 mm and 63.5 mm when in the expanded inflated configuration.

7. A catheter according to claim 1 wherein the heat exchange balloon has a diameter greater than 14 mm when in the expanded configuration.

8. A catheter according to claim 7 wherein the catheter is configured to deliver said at least 400 Watts of cooling power when operated within a rigid 22 mm ID tube through which water at a temperature of 37 degrees C. is pumped at a rate of 2.5 liters per minute.

9. A catheter according to claim 1 wherein the diameter of the heat exchange balloon when in the expanded configuration is at least 3.5 times larger than the diameter of the heat exchange balloon when in the collapsed configuration.

10. A catheter according to claim 1 further comprising a location detector for detecting when substantially the entire balloon has moved from a blood vessel of a first diameter into a blood vessel of a second diameter.

11. A system comprising a catheter according to claim 1 in combination with said extracorporeal device.

12. A system according to claim 11 wherein the thermal exchanged fluid is pulsed as it circulates through the heat exchange balloon.

13. A system according to claim 12 wherein a heat exchanging surface of the heat exchange balloon undergoes movement in response to the pulsing of the thermal exchange fluid without substantial deflation of the heat exchange balloon between pulses.

14. A system according to claim 13 wherein at least a portion of the heat exchange balloon is pre-tensioned to maintain a tensioned state that results in enhancement of the magnitude of movement of the heat exchange surface in response to the pulses.

15. A system according to claim 1 wherein the system is capable of delivering said at least about 400 watts of cooling power when the heat exchange balloon is positioned within a rigid 22 mm ID tube through which water at a temperature of 37 degrees C. is pumped at a rate of 2.5 liters per minute.

16. A system according to claim 1 further comprising a controller which receives user input of a target body temperature and feedback from a sensor that senses the subject's current body temperature, said controller being operative to vary one or more of:
  the temperature to which the thermal exchanger fluid is cooled;
  the flowrate of the thermal exchange fluid through the extracorporeal heat exchanger; and
  the flowrate of thermal exchange fluid through the heat exchange balloon;
to thereby cause the subject's sensed body temperature to be cooled to the target body temperature and to thereafter maintain the subject's sensed body temperature at or within a permissible range of the target temperature for a period of time.

17. A system according to claim 1 wherein the heat exchange balloon has a helical configuration.

18. A heat exchange catheter configured for connection to an extracorporeal device having a cooler which to cool a thermal exchange fluid that circulates through the heat exchange catheter, said heat exchange catheter comprising:
  a flexible catheter shaft having a proximal end, a distal end, an inflow lumen, an outflow lumen; and
  a heat exchange balloon connected to the inflow and outflow lumens such that, when the catheter is connected to said fluid cooling apparatus, thermal exchange fluid will circulate from the extracorporeal heat exchanger, through the inflow lumen, through the heat exchange balloon, through the outflow lumen and back to the extracorporeal heat exchanger;
  the heat exchange balloon being collapsible to a collapsed configuration such that a distal portion of the catheter shaft, inclusive of the heat exchange balloon in said collapsed configuration, is insertable into a human subject's vasculature through a tubular introducer that has an outer diameter no larger than 5 mm, said heat exchange balloon being thereafter expandable by circulation of thermal exchange fluid therethrough to an expanded configuration that has at least 125 cm² of blood contacting;
  the heat exchange balloon, when in said expanded configuration with cooled thermal exchange fluid being circulated therethrough, being capable of cooling blood flowing in heat exchange proximity to the heat exchange balloon at a power of a least 400 Watts.

19. A heat exchange catheter according to claim 18 wherein the heat exchange balloon has a wall thickness of less than 0.01651 mm.

20. A catheter according to claim 18 wherein the heat exchange balloon has a helical configuration.

21. A catheter according to claim 20 wherein the helical heat exchange balloon has at least helical twists per linear 304.8 mm of length.

* * * * *

UNITED STATES PATENT AND TRADEMARK OFFICE
CERTIFICATE OF CORRECTION

PATENT NO. : 10,940,035 B2  
APPLICATION NO. : 15/953116  
DATED : March 9, 2021  
INVENTOR(S) : Ben F. Brian and Scott D. Wilson Page 1 of 1

It is certified that error appears in the above-identified patent and that said Letters Patent is hereby corrected as shown below:

In the Specification

Column 1, Line 8 (approx.), delete "issuing" and insert -- issued --

In the Claims

Column 15, Line 11, Claim 1, delete "a" and insert -- at --

Column 16, Line 1, Claim 15, delete "system" and insert -- catheter --

Column 16, Line 6, Claim 16, delete "system" and insert -- catheter --

Column 16, Line 23, Claim 17, delete "system" and insert -- catheter --

Column 16, Line 53 (approx.), Claim 18, after of, delete "a" and insert -- at --

Signed and Sealed this  
Twenty-ninth Day of June, 2021

Drew Hirshfeld  
*Performing the Functions and Duties of the*  
*Under Secretary of Commerce for Intellectual Property and*  
*Director of the United States Patent and Trademark Office*